US007048686B2

(12) United States Patent
Kameya et al.

(10) Patent No.: US 7,048,686 B2
(45) Date of Patent: May 23, 2006

(54) ENDOSCOPE SYSTEM INCLUDING A COMMUNICATIONS FUNCTION

(75) Inventors: Takayuki Kameya, Tokyo (JP); Hitoshi Mizuno, Tokyo (JP)

(73) Assignee: Olympus Corporation (JP)

( * ) Notice: Subject to any disclaimer, the term of this patent is extended or adjusted under 35 U.S.C. 154(b) by 558 days.

(21) Appl. No.: 10/183,327

(22) Filed: Jun. 25, 2002

(65) Prior Publication Data

US 2003/0004397 A1    Jan. 2, 2003

(30) Foreign Application Priority Data

Jun. 28, 2001    (JP)    ............... 2001-196586

(51) Int. Cl.
*A61B 1/04* (2006.01)
*A61B 1/06* (2006.01)
*A61B 1/12* (2006.01)

(52) U.S. Cl. ............... 600/179; 600/102; 600/109; 600/158; 600/181

(58) Field of Classification Search ............... 600/101, 600/103, 109, 102, 160, 179, 178, 118, 158, 600/181; 348/65, 68, 71, 74, 76
See application file for complete search history.

(56) References Cited

U.S. PATENT DOCUMENTS

| | | | | |
|---|---|---|---|---|
| 4,633,304 A | * | 12/1986 | Nagasaki | 348/69 |
| 5,623,637 A | * | 4/1997 | Jones et al. | 711/164 |
| 5,701,904 A | * | 12/1997 | Simmons et al. | 600/301 |
| 5,761,144 A | * | 6/1998 | Fukuzumi | 365/226 |
| 6,184,922 B1 | * | 2/2001 | Saito et al. | 348/65 |
| 6,319,199 B1 | * | 11/2001 | Sheehan et al. | 600/200 |
| 6,452,626 B1 | * | 9/2002 | Adair et al. | 348/158 |
| 6,480,174 B1 | * | 11/2002 | Kaufmann et al. | 345/8 |
| 6,538,687 B1 | * | 3/2003 | Saito et al. | 348/65 |
| 6,561,428 B1 | * | 5/2003 | Meier et al. | 235/462.25 |
| 6,612,981 B1 | * | 9/2003 | Onishi et al. | 600/118 |
| 6,652,451 B1 | * | 11/2003 | Murata et al. | 600/118 |
| 2001/0051766 A1 | * | 12/2001 | Gazdzinski | 600/309 |
| 2002/0022763 A1 | * | 2/2002 | Sano et al. | 600/109 |
| 2002/0183590 A1 | * | 12/2002 | Ogawa | 600/117 |
| 2002/0184122 A1 | * | 12/2002 | Yamaguchi et al. | 705/30 |

FOREIGN PATENT DOCUMENTS

JP    7-327922    12/1995

* cited by examiner

*Primary Examiner*—John P. Leubecker
(74) *Attorney, Agent, or Firm*—Ostrolenk, Faber, Gerb & Soffen, LLP

(57) ABSTRACT

An endoscope system has an electronic endoscope, a signal processing section and a data transmitting and receiving section. The electronic endoscope has an image pickup element at a distal end portion of an insert section thereof to be inserted in a body. The other end portion of the endoscope is located outside the body. The signal processing section processes an image signal obtained by the image pickup element. The data transmitting and receiving section transmits and receives data to and from a network environment by radio.

38 Claims, 14 Drawing Sheets

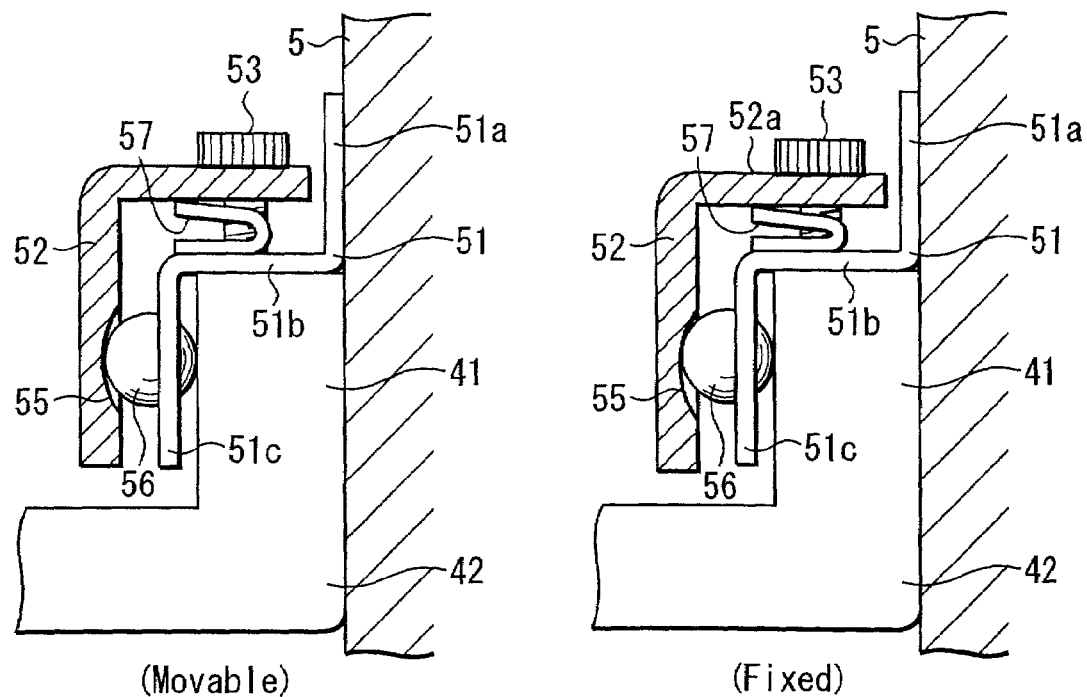
FIG. 10 (Movable)  FIG. 11 (Fixed)
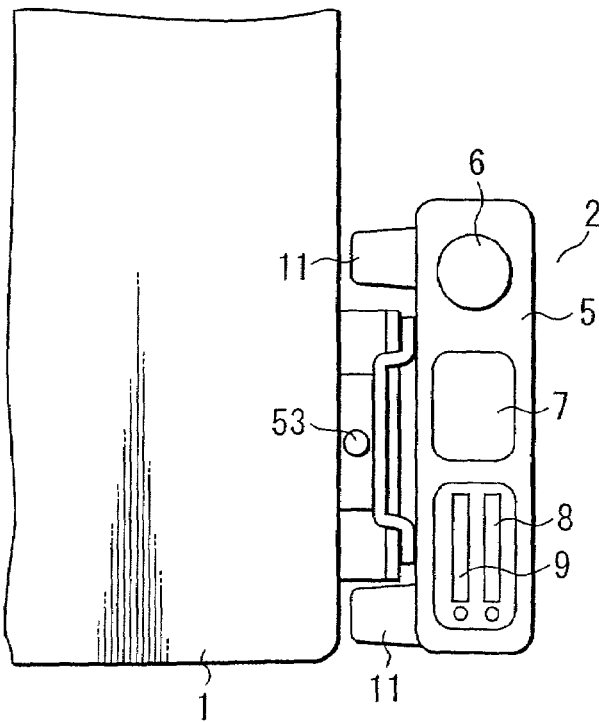
FIG. 12

ENDOSCOPE SYSTEM INCLUDING A COMMUNICATIONS FUNCTION

CROSS-REFERENCE TO RELATED APPLICATIONS

This application is based upon and claims the benefit of priority from the prior Japanese Patent Application No. 2001-196586, filed Jun. 28, 2001, the entire contents of which are incorporated herein by reference.

BACKGROUND OF THE INVENTION

1. Field of the Invention

The present invention relates to an endoscope system, in which an electronic endoscope and peripherals are well-combined.

2. Description of the Related Art

In a conventional endoscope system, an endoscope and peripherals, such as a light source device, a video processor and a monitor, are set in the same endoscope room. Diagnosis or operations using endoscopes lie in the field of medical treatments that are performed in a large medical facility, for example, a hospital provided with sufficient equipment and staffs. Previously, it was difficult to perform treatment or diagnosis at home or in a small private medical office, or during a disaster-related rescue, or perform group examination away from a medical facility, or perform medical examination on an island.

At a disaster site, if diagnosis with an endoscope is possible, appropriate medical treatment can be administered. Further, if doctors are informed of diagnosis results before arriving at the scene, on-the-spot treatment may be performed as soon as the doctor arrives.

BRIEF SUMMARY OF THE INVENTION

An object of the present invention is to provide an endoscope system in which a communications function is provided, allowing medical treatment to be carried out in understaffed, ill-equipped or difficult conditions, such as in home cares or at disaster sites.

To achieve the above object, an endoscope system according to the present invention comprises:

an endoscope including an image pickup element which picks up an image inside a body;

a processing device which processes a signal obtained through the image pickup element and generating an image signal; and a data transmitting and receiving device for transmitting and receiving data including the image signal to and from a network environment set outside the body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 10 is a longitudinal cross-sectional view of the support mechanism of the processor unit of the endoscope system according to the first embodiment in a slidable state;

FIG. 11 is a longitudinal cross-sectional view of the support mechanism of the processor unit of the endoscope system according to the first embodiment in a fixed state;

FIG. 12 is a plan view of a processor unit of an endoscope system according to a second embodiment of the present invention attached to a bedside;

DETAILED DESCRIPTION OF THE INVENTION

FIRST EMBODIMENT

An endoscope system set to a bedside according to a first embodiment of the present invention will be described with reference to FIGS. 1 to 11.

Figure 1:
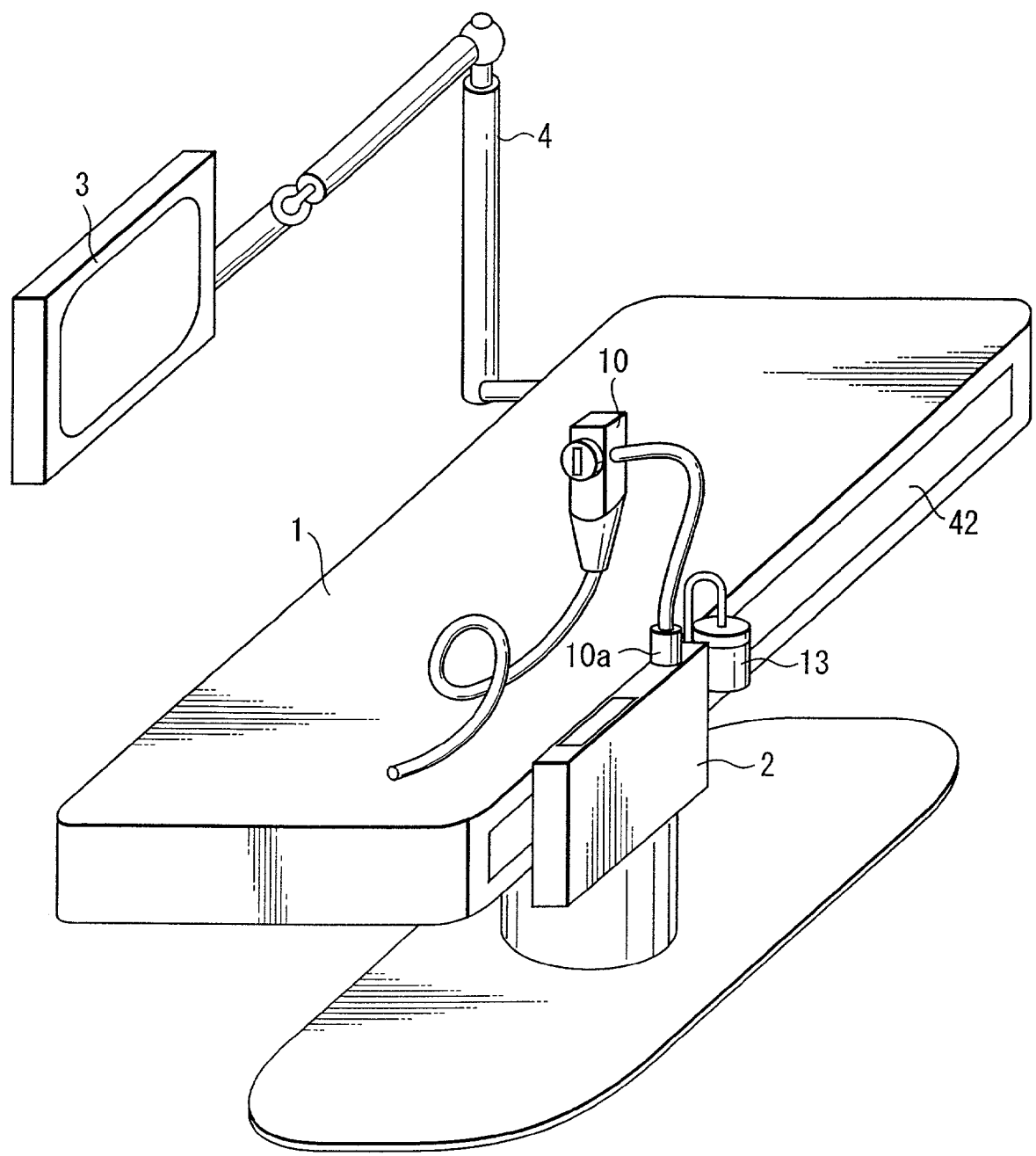
FIG. 1 is a perspective view of an endoscope system according to a first embodiment of the present invention.

In FIG. 1, reference numerals 1 and 2 respectively denote a patient bed and a processor unit for an endoscope. The processor unit 2 is portable, and it is detachably set to a peripheral portion, such as a side frame, of the bed 1. In this embodiment, it is detachably set to a side frame on one side of the bed 1 via a support mechanism described later. A monitor 3, such as a CRT, is attached to the side frame on the other side of the bed 1 via a support arm 4.

Figure 4:
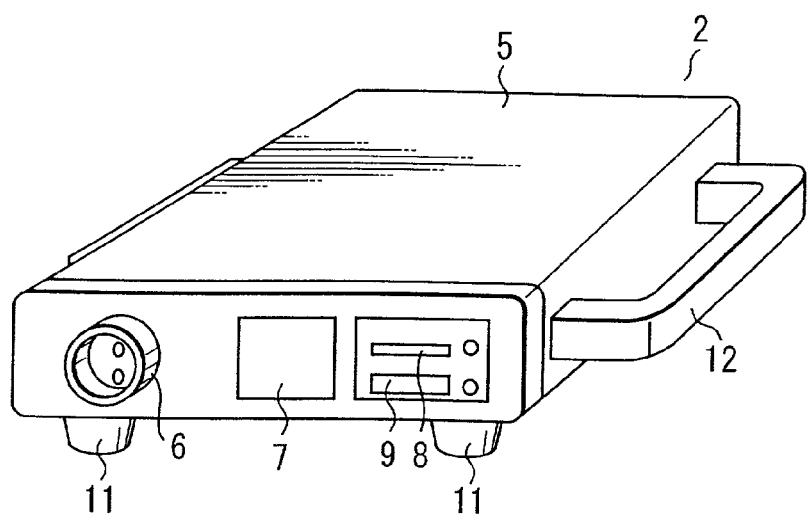
FIG. 4 is a perspective view of a processor unit of the endoscope system according to the first embodiment set on a table.
Figure 5:
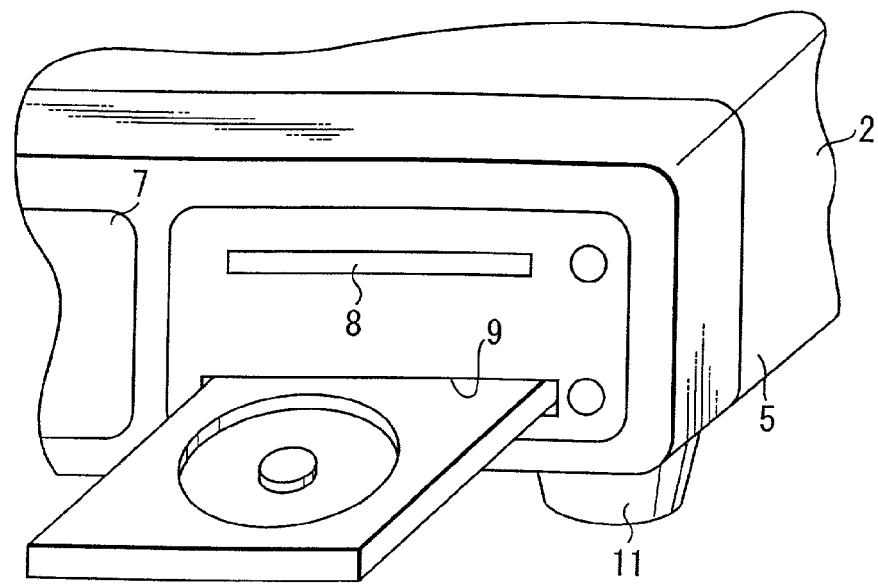
FIG. 5 is a perspective view showing a part of the processor unit of the endoscope system according to the first embodiment.

As shown in FIG. 4, the processor unit 2 has a flat box-shaped outer case 5, which incorporates various functional components. A side surface perpendicular to the longest width direction of the outer case 5 includes an endoscope connecting section 6, an operation panel section 7, a memory card inlet/outlet port 8 adjacent to the operation panel 7, and an inlet/outlet port 9 for a writable memory medium (CD-R) or an optionally rewritable versatile memory medium (CD-RW). A connector 10a of an endoscope 10, to be described later, is connected to the endoscope connecting section 6.

As shown in FIG. 4, a plurality of legs 11 to be placed on a table are formed on a surface perpendicular to the shortest width direction of the outer case 5. A handle 12 is attached to a side adjacent to the surface having the legs.

Figure 6:
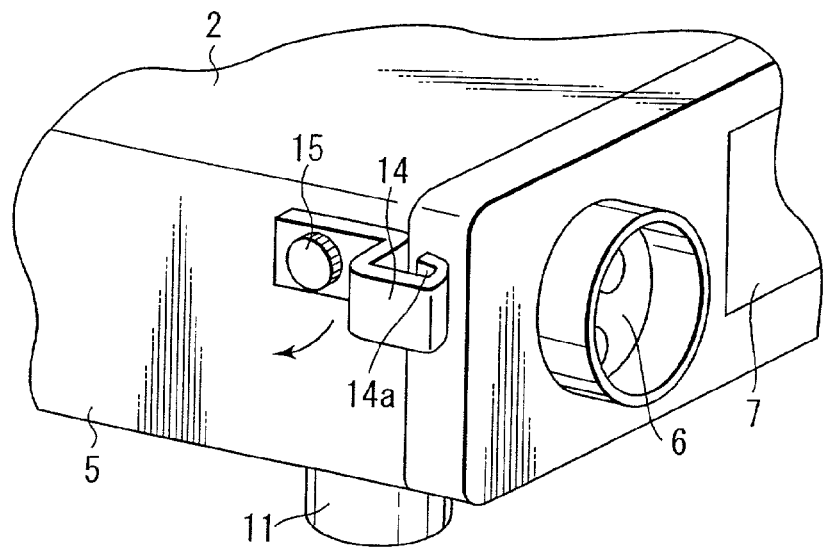
FIG. 6 is a perspective view showing another part of the processor unit of the endoscope system according to the first embodiment.
Figure 7:
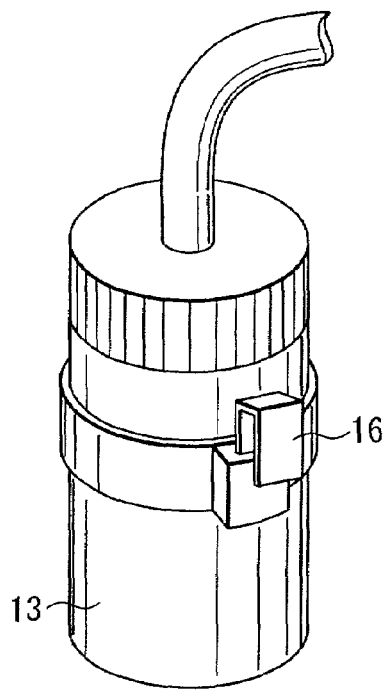
FIG. 7 is a perspective view of a water supply tank to be connected to the processor unit of the endoscope system according to the first embodiment.

As shown in FIG. 6, a hook 14 to be engaged with a water supply tank 13 shown in FIG. 7 is attached to a side opposite to the side having the handle 12. The hook 14 is fixed to the outer case 5 by a threaded knob 15. When the knob 15 is loosened, the hook 14 can be rotated in the direction of the arrow shown in FIG. 6, so that the direction of an engaging groove 14a of the hook 14 can be changed.

FIG. 6 shows a state in which the processor unit 2 is placed on the upper surface of a table by utilizing the legs 11. In this state, an engagement fitting 16 of the water supply tank 13 is inserted into the engaging groove 14a of the hook 14, so that the water supply tank 13 can be set in the normal direction.

Figure 2:
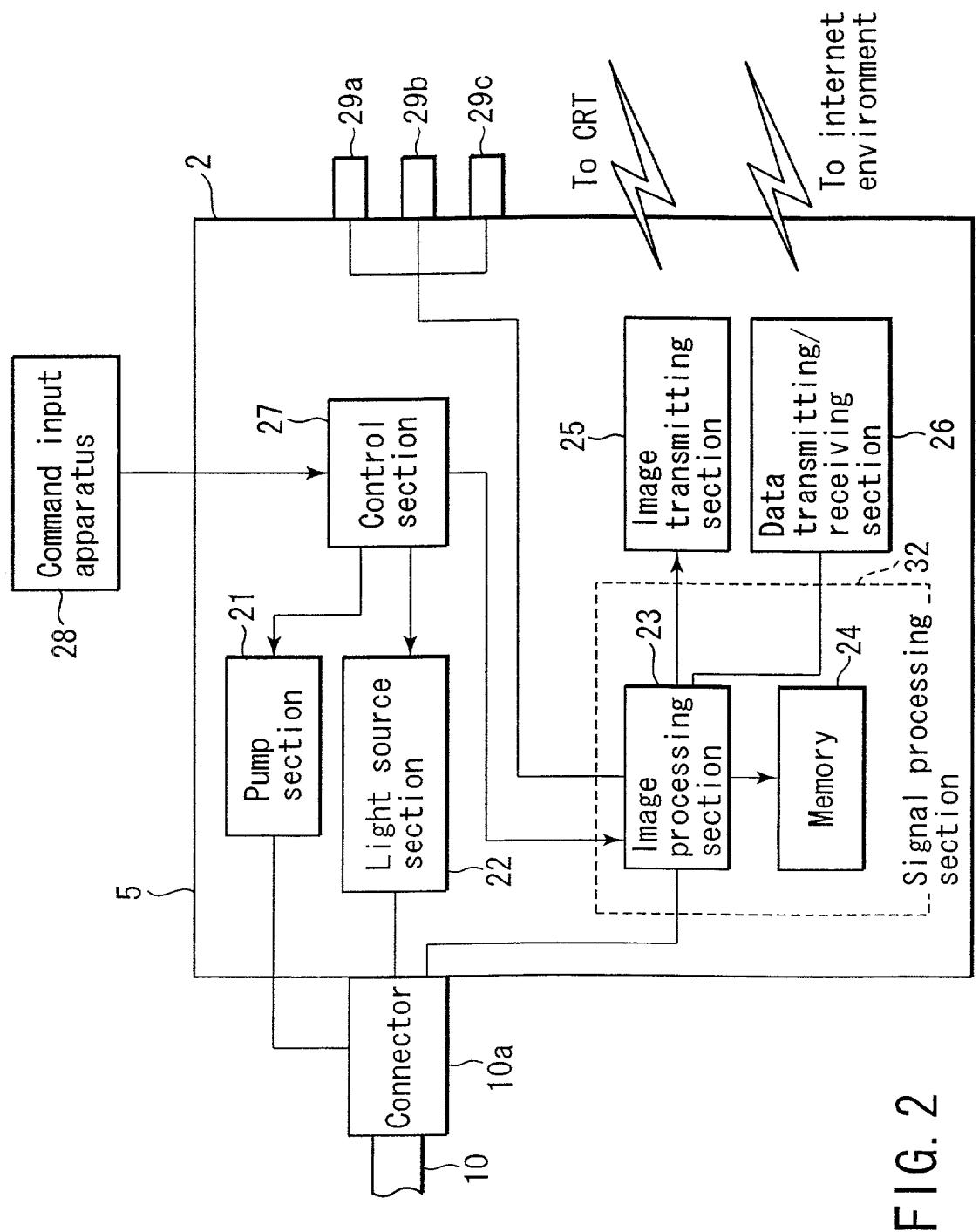
FIG. 2 is a block diagram of an endoscope processor of the endoscope system according to the first embodiment.

The processor unit 2, as shown in FIG. 2, includes a pump section 21, a light source section 22, an image processing section 23, a memory 24, an image transmitting section 25, a data transmitting and receiving section 26, and a control section 27 for controlling these sections. The control section 27 receives commands input through a command input apparatus 28, such as a keyboard of the operation panel section 7. Further, various commands can be input to the control section 27 through an additional keyboard or the like (not shown).

As shown in FIG. 2, a plurality of output terminals 29 are arranged to an outer surface of the processor unit 2. The output terminals 29 include an IEEE 139 interface terminal, for example, a Sony iLink system terminal 29a, a USB (2.0) terminal 29b and a video output terminal 29c. These terminals are connected to an electric communication circuit by wires; however, they can be wirelessly connected to an electric communication circuit by another transmission means.

The pump section 21 is connected to the water supply tank 13 via the connector 10a of the endoscope 10 coupled to the endoscope connecting section 6. When the interior of the water supply tank 13 is pressurized, the water contained therein is supplied to a water supply channel (not shown) of the endoscope 10. Thus, the endoscope 10 is supplied with water. Functions for supplying air and water to the endoscope 10 can be switched by means of a switch (not shown) provided on the endoscope 10. The light source section 22 supplies illuminating light to a light guide (not shown) of the endoscope 10 connected to the endoscope connecting section 6.

The image processing section 23 of the processor unit 2 processes a signal obtained by an image pickup element (not shown) mounted at a top end of an insert section of the endoscope 10, and coverts it to an image signal. The image signal can be stored in the memory 24, and transmitted by radio to the monitor 3, such as the CRT, via the image transmitting section 25, so that it can be displayed on the monitor 3. The image signal converted by the image processing section 23 can also be transmitted by radio to a LAN/Internet environment through the data transmitting and receiving section 26. The radio transmission can be performed between the endoscope system and a personal computer in a hospital, by utilizing communication in conformity with BLUETOOTH™, which is a standard for bi-directional communications by radio among various apparatuses in a frequency band that can be used without a license.

The image processing section 23 and the memory 24 are components of a signal processing section 32. The storage medium inserted through the memory card inlet/outlet port 8 or the CD-R (CD-RW) inlet/outlet port 9 may be utilized as the memory 24.

Figure 8:
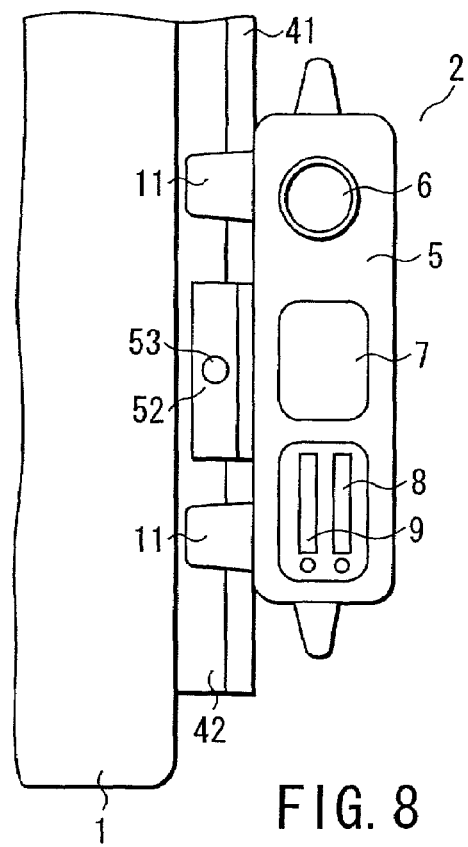
FIG. 8 is a plan view of the processor unit of the endoscope system according to the first embodiment attached to a bedside.

A support mechanism for supporting the processor unit 2 is provided on a side portion of the bed 1. The support mechanism is slidably held to the bed 1. As shown in FIG. 8, the support mechanism is constructed as follows. A side portion of the bed 1 includes a guide 42 extending in the longitudinal direction of the bedside. The projected end of the guide 42 forms an upright portion 41. As shown in FIGS. 10 and 11, a support frame 51 having a crank-shaped cross section is provided on that surface of the outer case 5 of the processor unit 2, on which the legs 11 to be placed on a table are formed. The support frame 51 is engaged with the upright portion 41, such that an upper portion 51a of the support frame 51 is adhered to the outer surface of the outer case 5, a middle portion 51b thereof is placed on the upper end of the upright portion 41 of the guide 42, and a lower portion 51c thereof faces the inner surface of the upright portion 41.

Figure 9:
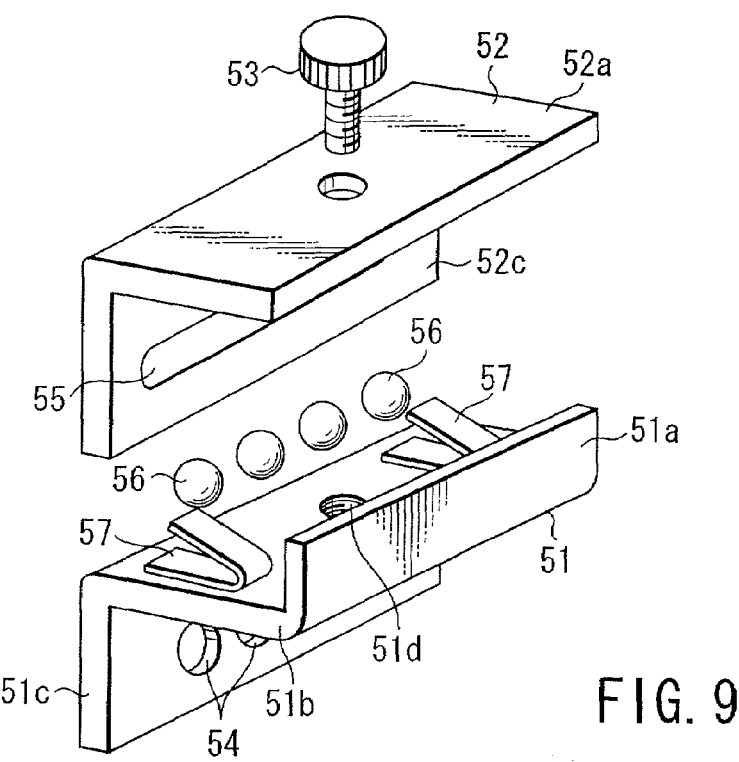
FIG. 9 is an exploded perspective view of a support mechanism for attaching the processor unit of the endoscope system according to the first embodiment to a bedside.
Figure 13:
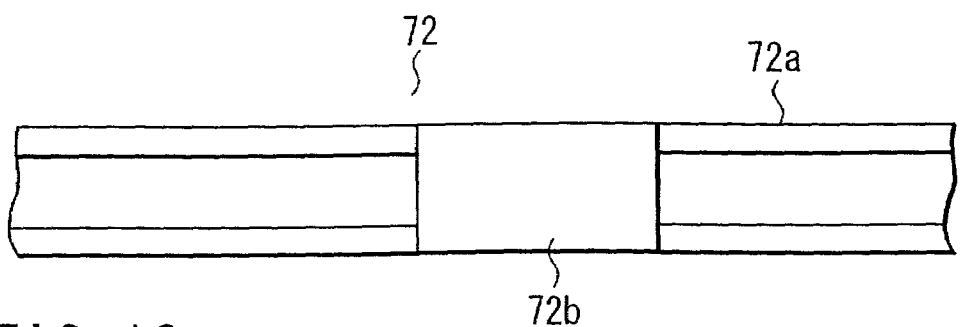
FIG. 13 is a front view of a slide rail of a support mechanism of the endoscope system according to the second embodiment.

As shown in FIG. 9, the support frame 51 has a fixing part 52 made of a plate material having an L-shaped cross section. A fastening screw 53 is inserted through a side of the fixing part 52. An end screw portion of the fastening screw 53 can be screwed into a screw hole 51d formed in the middle portion 51b of the support frame 51. A plurality of holes 54, aligned in a sliding direction, are formed in the lower portion 51c of the support frame 51. An elongated groove 55 is formed in a lower portion 52c of the fixing part 52 along the direction in which the holes 54 are aligned. Balls 56 are fitted into the respective holes 54 in the support frame 51. The balls 56 are also partly fitted into the groove 55 of the fixing part 52. Elastic members 57, such as springs, are inserted between the middle portion 51b of the support frame 51 and an upper portion 52a of the fixing part 52. The fixing part 52 is urged upward by elastic restoring force of the elastic members 57.

As shown in FIG. 10, when the fastening screw 53 is loosened, the fixing part 52 is moved upward by the elastic restoring force of the elastic members 57 and the balls 56 are engaged with a deepest portion in a central portion of the groove 55 of the fixing part 52. Therefore, the balls 56 do not press the inner surface of the upright portion 41 of the guide 42. In this state, the support frame 51 is-movable together with the processor unit 2 along the upright portion 41 of the guide 42.

As shown in FIG. 11, when the fastening screw 53 is fastened to the support frame 51, the fixing part 52 presses the elastic members 57 and moves down against the elastic restoring force. Since the fixing part 52 lowers, the balls 56 are deviated from the central portion of the groove 55 of the fixing part 52. For this reason, the balls 56 are pressed against the inner surface of the upright portion 41 of the guide 42 by a wedging function of the groove 55, with the result that the support frame 51 is fixed to the upright portion 41 of the guide 42. Thus, the processor unit 2 is fixed at that portion. In this way, the processor unit 2 can be moved along the guide 42 to a desired position and fixed at that position.

Figure 3:
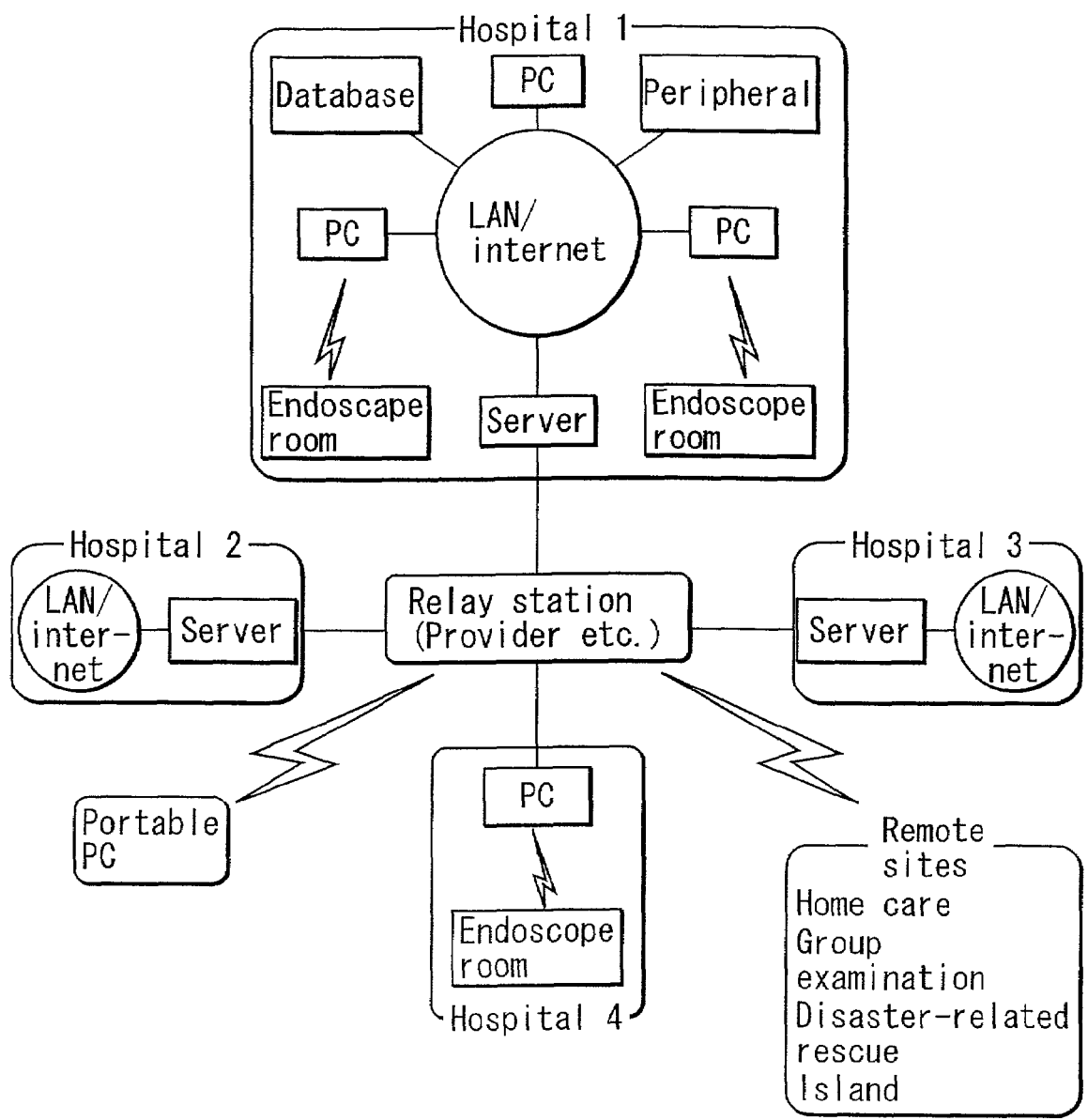
FIG. 3 is a schematic diagram of a network in a case where the endoscope system according to the first embodiment is set in an endoscope room of a hospital.

A concept of a network, in which the endoscope system is set in an endoscope room of a hospital, will be described below with reference to FIG. 3. In FIG. 3, hospitals 1–3 are relatively large medical facilities, in which a network is constructed. A hospital 4 is a small private medical office. In general, no network is constructed in such a small medical office.

Image information obtained in an endoscope room of a hospital is transmitted by radio to a specific personal computer (PC). When a doctor receives the information, he or she performs an image diagnosis and returns instructions including remarks and details of the treatment to an inspector in the endoscope room. During the diagnosis, the doctor can refer to past cases stored in the database. It is possible to send the image to another hospital or refer to the database of another hospital via a provider or the like.

When the endoscope system is set in a treatment room of the hospital (small private medical office) 4, an image obtained by the system can be sent to the large hospital 1, 2 or 3, to ask them for a diagnosis. As a result, a diagnosis or treatment can be performed at the same accuracy as that in the large hospital. Further, it is possible to send a diagnostic image to the hospital where the patient is to be transported, in order to confirm whether the patient can be accepted there (whether the necessary treatment can be performed in the hospital).

When the endoscope system of the present invention is used at remote sites away from a medical facility, for example, a home, group examination, an island or a disaster-related rescue, the image obtained at the scene may be transmitted to a large hospital via a relay station, so that an accurate diagnosis can be made.

Moreover, if the situation is transmitted via a relay station to the portable computer of a doctor on the move to the scene of a disaster or a hospital where the patient is to be transported, an appropriate treatment may be performed as soon as the doctor arrives at the hospital.

The endoscope system according to the embodiment of the present invention has a radio communication function. Therefore, it can transmit an observation image by radio to a facility where diagnosis is possible (including the inside of the hospital) via a personal computer and the Internet, and receive diagnosis results and instructions for a treatment, etc., in return.

The endoscope system of the present invention and a personal computer inside the hospital can bi-directionally communicate with each other by radio link technology, such as BLUETOOTH™. In addition, since the processor unit 2 comprises the terminals 29, such as the Sony iLink system terminal 29a, the USB terminal 29b and the video output terminal 29c, it can be wire-connected to the network via the terminals.

As described above, since private medical offices and large hospitals are networked, even a doctor in private practice can provide the same medical treatment as that provided by the large hospitals.

Further, according to the above embodiment, the endoscope system is attached to the bedside and the processor unit 2 including the light source and image processor is movably set to a side surface of the patient bed 1. Therefore, the processor unit 2 is moved horizontally along the bed 1 in accordance with the body part to be inspected, so that it can be set to the best-suited position.

Furthermore, since the processor unit 2 incorporates the device for writing/reading information in/from an information recording medium, which can be physically inserted and drawn, the processor unit can easily read and write information.

SECOND EMBODIMENT

An endoscope system set to a bedside according to a second embodiment of the present invention will be described with reference to FIGS. 12 to 17. This embodiment uses another type of support mechanism for detachably attaching the endoscope processor unit 2 to a side frame of the patient bed 1.

In the support mechanism of the first embodiment, the guide 42 is projected from the side surface of the patient bed 1 throughout its length. According to the second embodiment, a recess 71 is formed in a side wall of the bed 1 and a slide rail 72 is arranged inside the recess 71. Therefore, the slide rail does not project from the side surface of the bed 1. The recess 71 extends horizontally along the side of the bed 1. The slide rail 72 has a fixed rail 72a fixed to an inmost wall of the recess 71 and a movable rail 72b movable horizontally along the fixed rail 72a.

Figure 14:
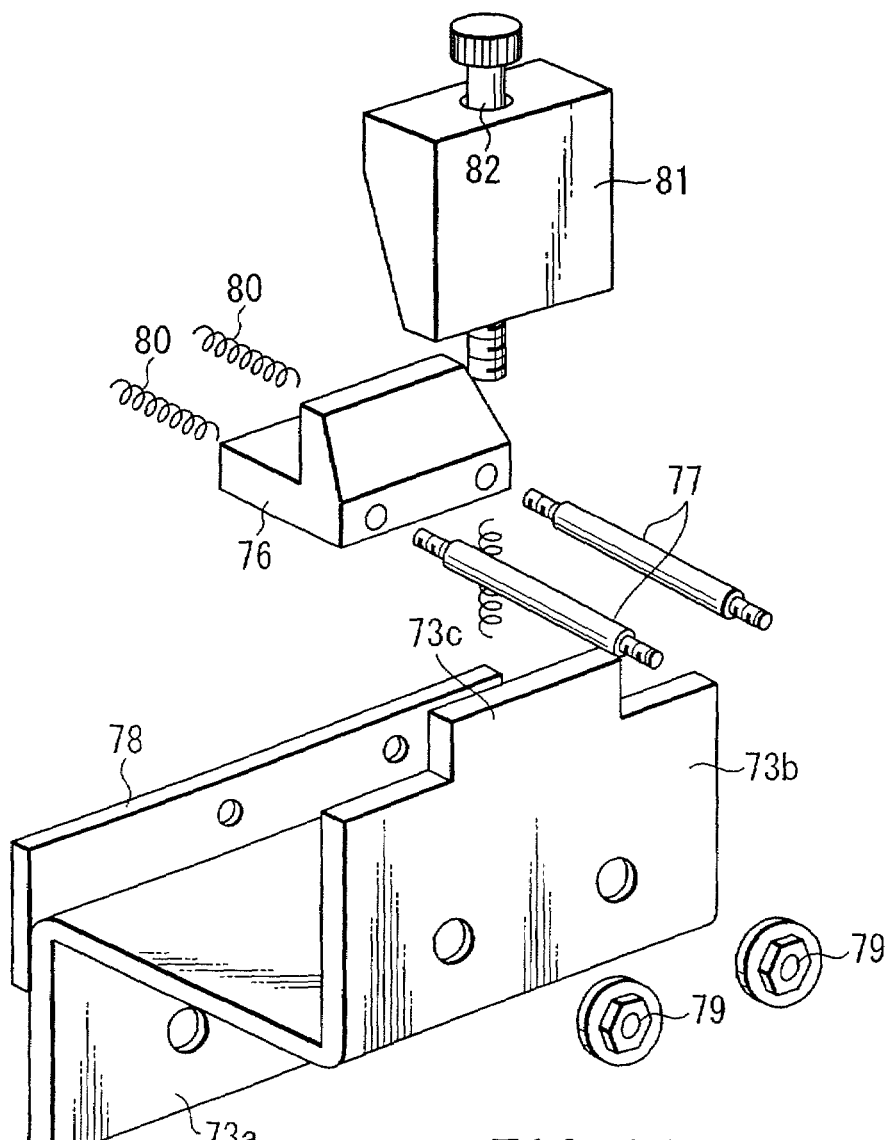
FIG. 14 is an exploded perspective view of the support mechanism of the endoscope system according to the second embodiment.
Figure 15:
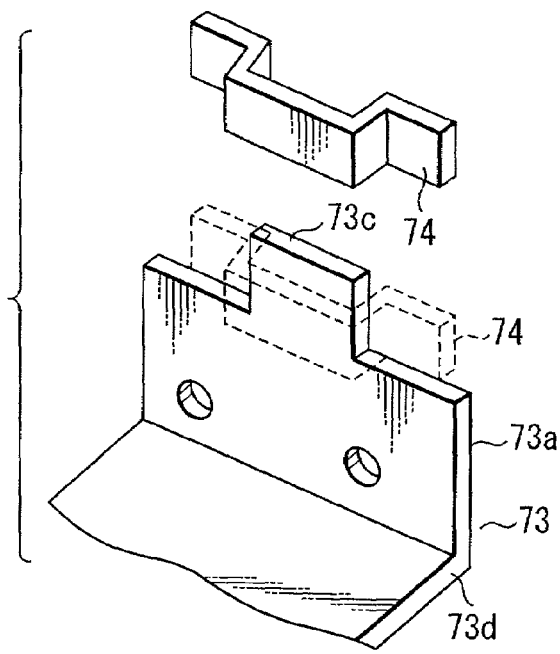
FIG. 15 is an exploded perspective view of a part of the support mechanism of the endoscope system according to the second embodiment.
Figure 16:
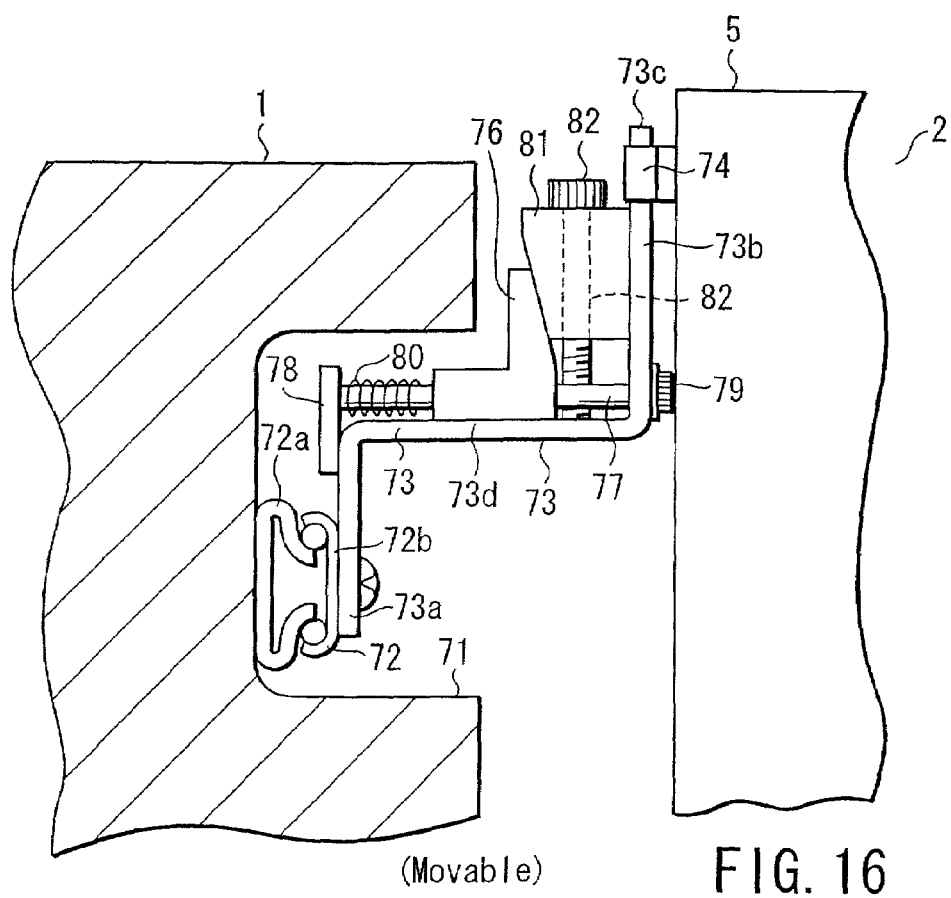
FIG. 16 is a longitudinal cross-sectional view of the support mechanism of the processor unit of the endoscope system according to the second embodiment in a movable state.

A support frame 73 is attached to the movable rail 72b of the slide rail 72. As shown in FIG. 14, the support frame 73 is made of a member having a crank-shaped cross section. A lower portion 73a of the support frame 73 is fixed to the movable rail 72b by screws. An upper portion 73b of the support frame 73 has a narrow engaging portion 73c. As shown in FIG. 15, the hook 74 attached to the outer case 5 of the processor unit 2 is inserted in and engaged with the engaging portion 73c of the support frame 73. Thus, the processor unit 2 can be supported by the support frame 73 of the support mechanism.

A slidable fixing block 76 is mounted on the upper surface of a horizontal middle portion 73d of the support frame 73. Two guide rods 77 are inserted in the fixing block 76, so that the block 76 can be guided by the two guide rods 77. One end of each guide rod 77 is screwed to a support piece 78 fixed to the lower portion 73a of the support frame 73. The other end of the guide rod 77 is inserted through the upper portion 73b of the support frame 73 and fixed thereto by a nut 79. Thus, the guide rods 77 are fixed to the support frame 73.

The fixing block 76 is horizontally movable along the guide rods 77 so as to freely contact to or separate from the upper portion 73b of the support frame 73. Coil springs 80 are wound around the guide rods 77 in the region between the support piece 78 and the fixing block 76. Owing to the elastic restoring force of the coil springs 80, the fixing block 76 is pressed toward the rear surface of the upper portion 73b of the support frame 73 (see FIG. 16).

Figure 17:
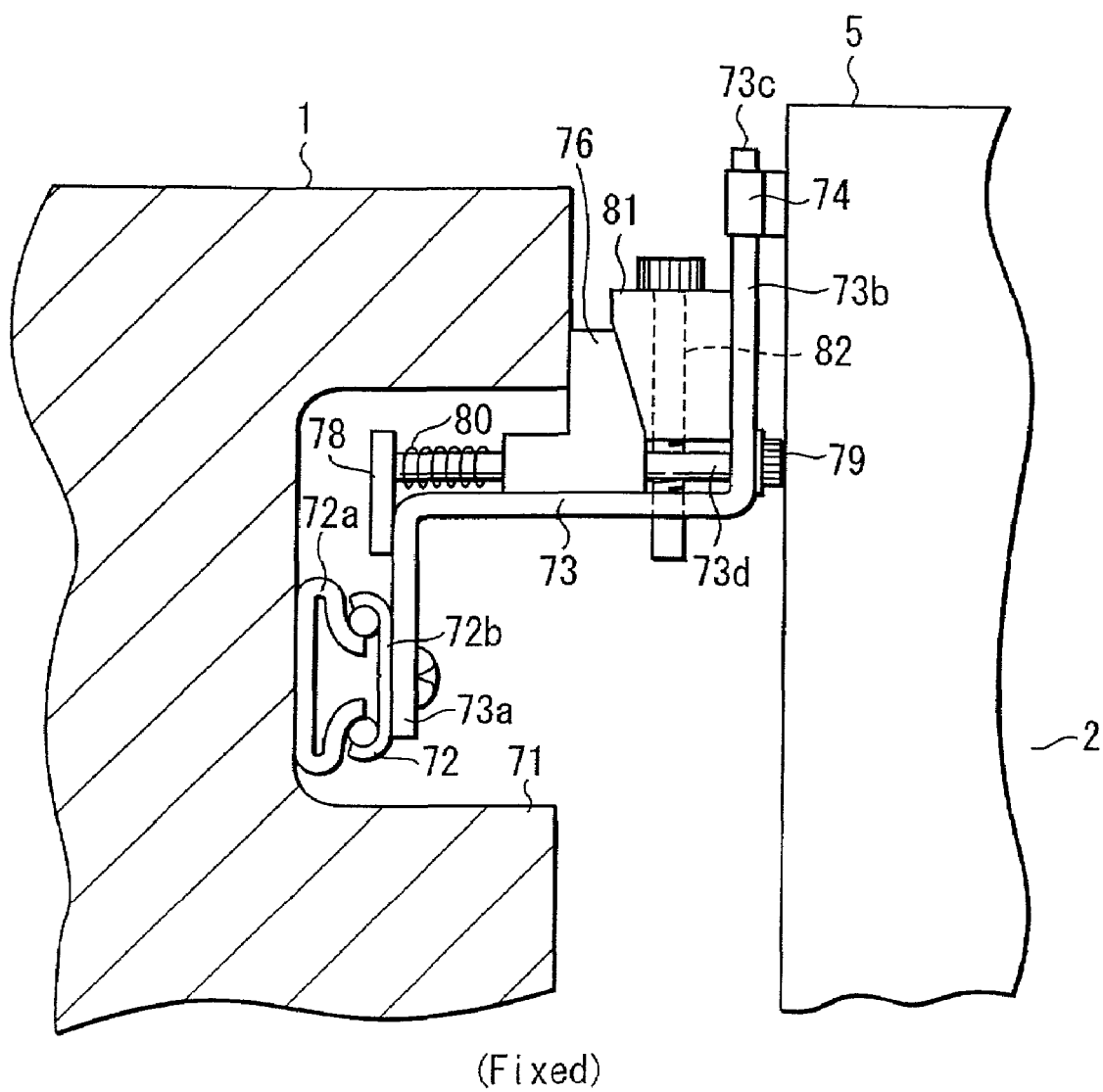
FIG. 17 is a longitudinal cross-sectional view of the support mechanism of the processor unit of the endoscope system according to the second embodiment in a fixed state.

A wedge member 81 is inserted between the fixing block 76 and the upper portion 73b of the support frame 73. A fastening screw 82 is inserted through the wedge member 81. When the fastening screw 82 is screwed into the horizontal middle portion 73d of the support frame 73 to push the wedge member 81 down, the fixing block 76 is moved back toward the support piece 78 by the wedging function. As shown in FIG. 17, when the fixing block 76 is moved back by the wedge member 81 the fixing block 76 is pressed against the side surface of the patient bed 1. Thus, the support frame 73 is fixed at this portion. In this way, the support mechanism can move the processor unit 2 to a desired position and fixed at that position by means of the support frame 73.

In this embodiment, only the support frame 73 for supporting the processor unit 2 projects from the side of the bed 1. Since the entire portion of the slide rail 72 supporting the support frame 73 is arranged inside the recess 71, the long slide rail 72 does not obstruct operations or the like.

THIRD EMBODIMENT

A hand-held endoscope system according to a third embodiment of the present invention will be described with reference to FIGS. 18 to 24.

Figure 18:
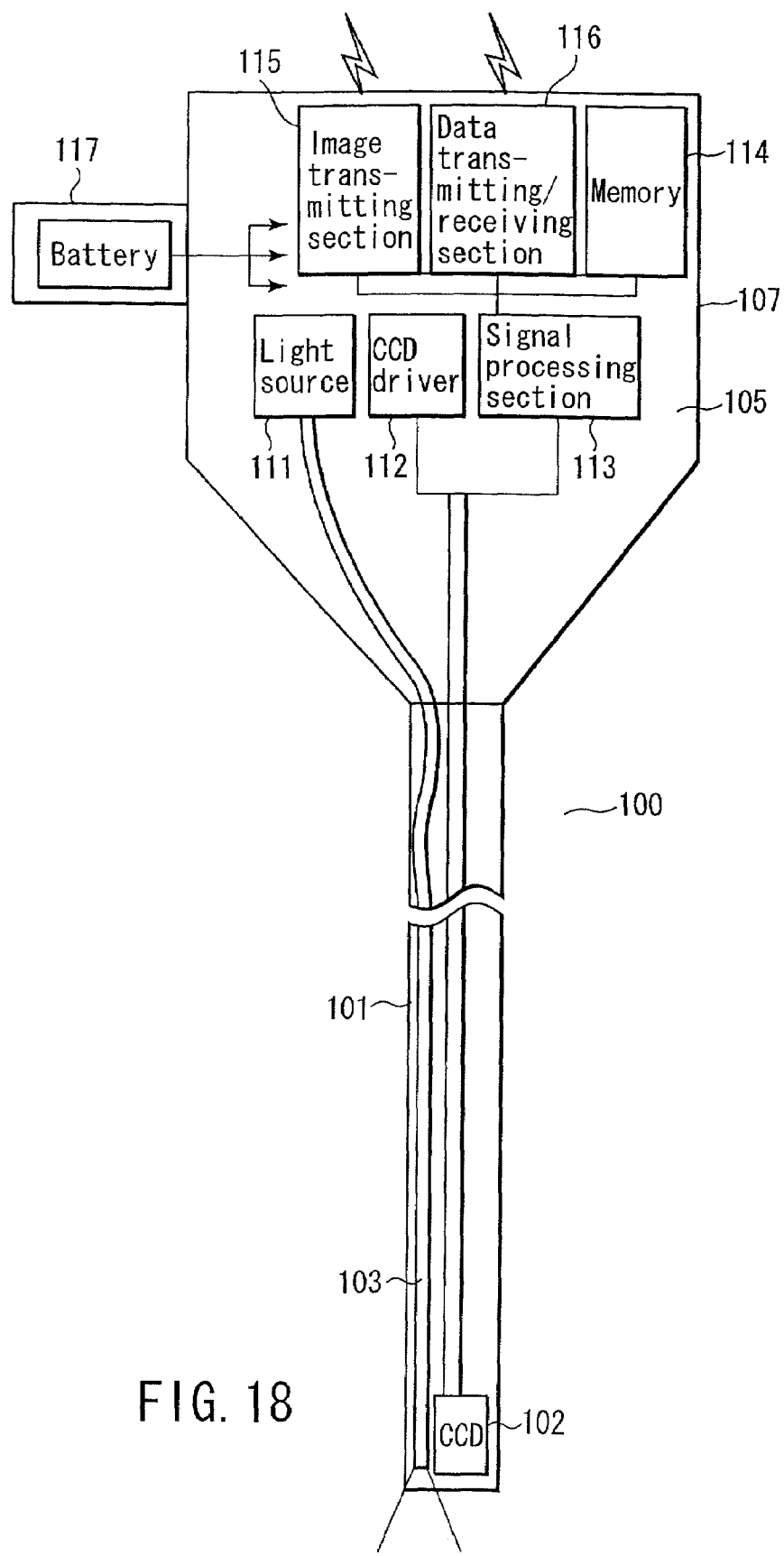
FIG. 18 is a block diagram of a hand-held endoscope system according to a third embodiment of the present invention.

As shown in FIG. 18, an endoscope 100 of the endoscope system of this embodiment has an insert section 101, which is inserted in a body cavity. An image pickup element 102 is located at the distal end of the insert section 101. The image pickup element 102 takes pictures of images in the body cavity. A light guide 103 is arranged in the insert section 101. Illuminating light supplied through the light guide 103 is output to the body cavity where the insert section 101 is inserted, thereby illuminating the field of vision.

A control unit 106 is detachably attached to a holding section (operating section) 105 of the endoscope 100. The control unit 106 includes, in its outer case 107, a light source 111 having an LED or the like, a CCD driving section 112, a signal processing section (image processing section) 113, a memory 114, an image transmitting section 115, a data transmitting and receiving section 116 and a control section (not shown) for controlling these sections. The light source 111, for example, an LED, may be arranged at the distal end portion of the insert section 101.

Figure 19:
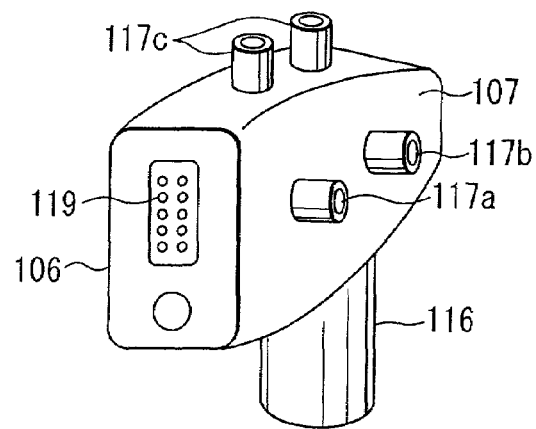
FIG. 19 is a perspective view showing a control unit of the endoscope system according to the third embodiment.
Figure 20:
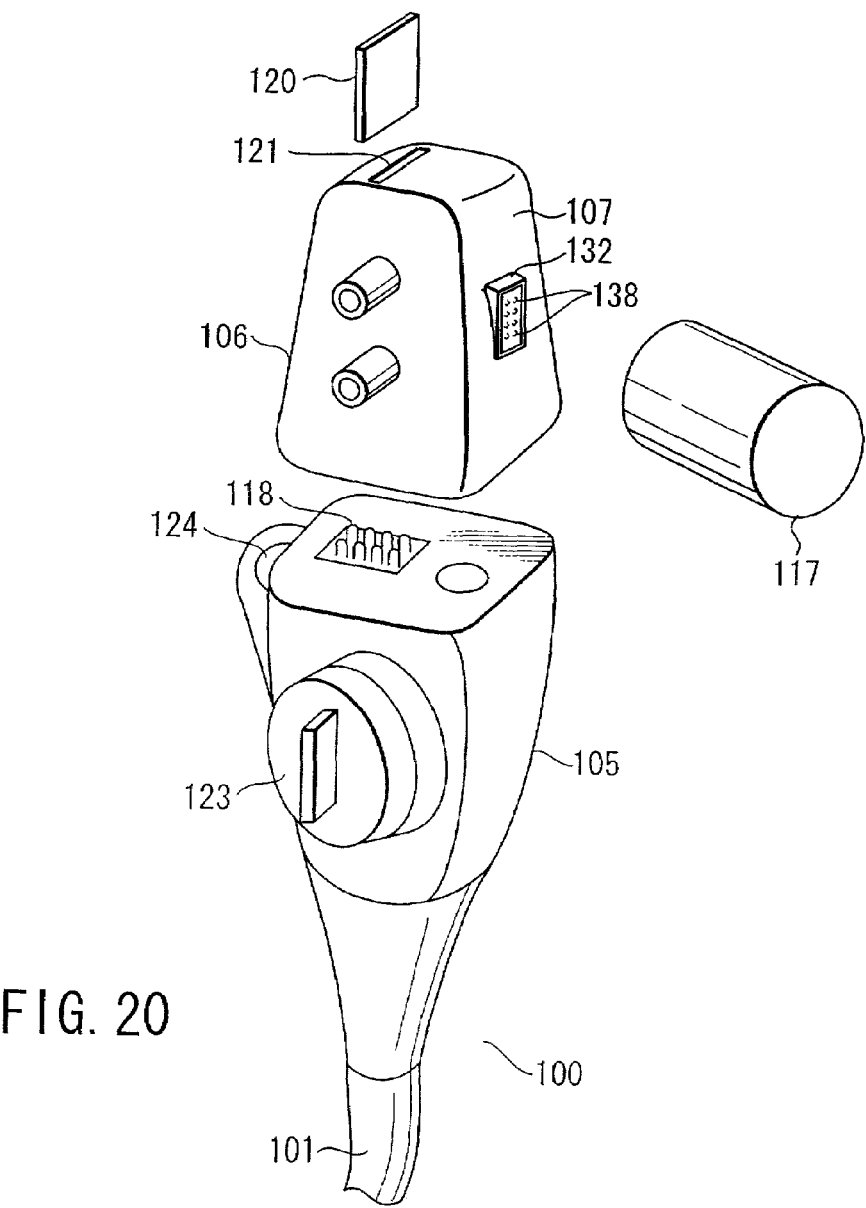
FIG. 20 is a perspective view showing the endoscope and the control unit of the endoscope system according to the third embodiment.

As shown in FIG. 20, a battery 117 is detachably attached to the outer case 107. The outer case 107 is connected to the holding section 105 of the endoscope 100. As shown in FIGS. 19 and 20, the holding section 105 and the outer case 107 respectively have connectors 118 and 119 for electrically connecting them. As shown in FIG. 20, an angle knob 123 and a treatment tool insertion port 124 are formed in the holding section 105 of the endoscope 100.

As shown in FIG. 18, the signal processing section (image processing section) 113 processes a signal obtained by the image pickup element 102 provided in the distal end of the insert section of the endoscope 100 to convert it to an image signal. The image signal can be stored in the memory 114, and transmitted by radio to a monitor, such as a CRT, via the image transmitting section 115, so that it can be displayed on the monitor. The image signal converted by the signal processing section 113 can also be transmitted by radio to a LAN/Internet environment through the data transmitting and receiving section 116. For example, the transmission can be performed in conformity with BLUETOOTH™.

Further, as shown in FIG. 19, the outer case 107 has output terminals for wire connection. The output terminals include an iLink system terminal 117a, a USB terminal 117b and a video output terminal 117c. The outer case 107 has an inlet/outlet port 121 for a memory card 120 (see FIG. 20) or a CD-R (CD-RW) inlet/outlet port. The storage medium inserted through such a port may be utilized as the memory 114.

The monitor of the endoscope of this system is not limited to that set to another part of the bedside as in the first embodiment, but may of a type attached to the outer case 107 of the control unit 106. In this case, the monitor may be of built-in type, or separate type, which is externally connected to the outer case 107.

In addition, an air tank or air supply unit may be attached to the outer case 107 of the control unit 106. In this case also, the air tank may be of built-in type or separate type. Further, an air/water supply unit may be connected to the control unit 106 through a cable. Alternatively, the air/water supply unit may be connected to the holding section 105.

Figure 21:
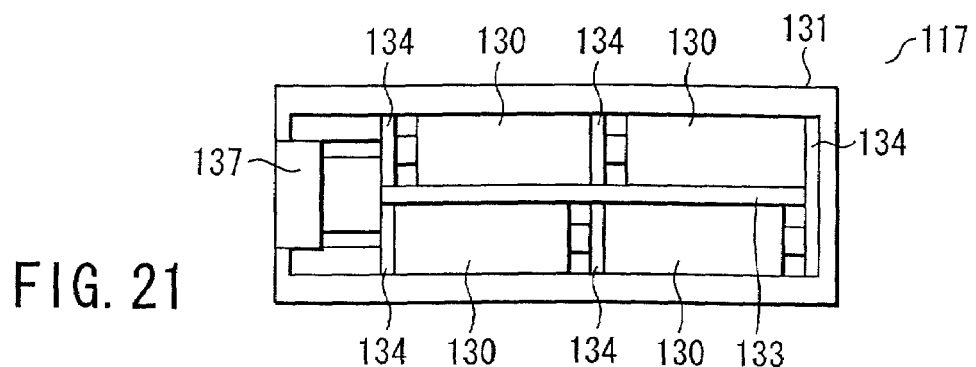
FIG. 21 is an illustrative diagram showing an internal structure of a battery of the endoscope system according to the third embodiment.
Figure 22:
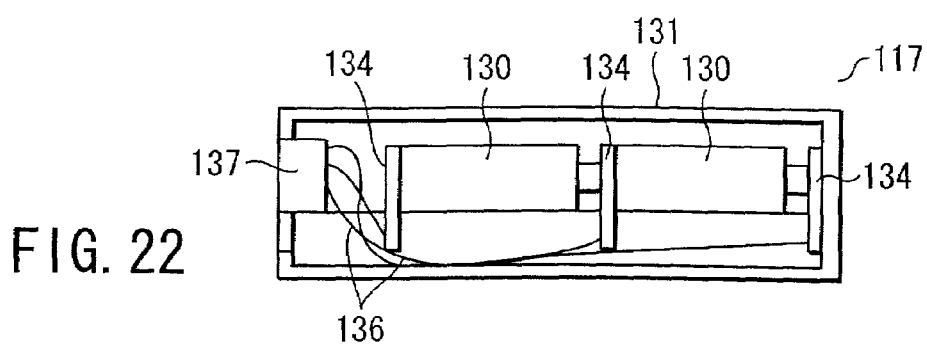
FIG. 22 is an illustrative diagram showing an internal structure of the battery of the endoscope system according to the third embodiment.
Figure 23:
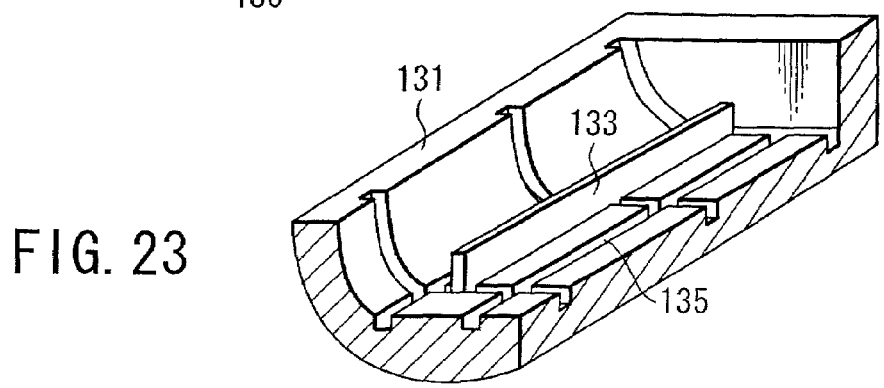
FIG. 23 is a perspective view of an outer case of the battery of the endoscope system according to the third embodiment.

The outer case 107 has a connector 132 for connecting a battery. The battery 117 is connected to the connector 132. As shown in FIGS. 21 to 23, the battery 117 is constituted by a plurality of cells 130 arranged in two rows in a case 131, with an insulating plate 133 interposed between the rows. Metal plates 134 are arranged between the cells 130 and at both ends of the cells. Grooves 135 are formed in the inner wall of the case 131. The insulating plate 133 and the metal plates 134 are positioned in the case 131 with the edge portions thereof being fitted in the grooves 135.

As shown in FIG. 22, leads 136 are respectively connected to the metal plates 134. The leads are individually connected to terminals of a connector 137. The value of the output voltage can be changed in accordance with a selected terminal of the connector 137. Therefore, each of the functional components of the control unit 106 is connected to a connector terminal coupled to a terminal 138, which is suited for a voltage adapted for the component, so that it can be supplied with a suitable voltage.

In the endoscope system of this embodiment, since the control unit 106 containing the light source section and the image processing section is attached to the holding section of the endoscope 100, the functional components are integrated in the endoscope 100. A few functional components are independent of the endoscope 100; however, since they are light and compact, the inspector can easily carry them.

If an LED is used as the light source, it may be a white LED or Red-green-blue LED. Further, a selective-type air/water supply unit may be used. The display may be of built-in type or separate type. Since the video output terminal 117c is provided, an image can be displayed in an external CRT, or the like.

Figure 24:
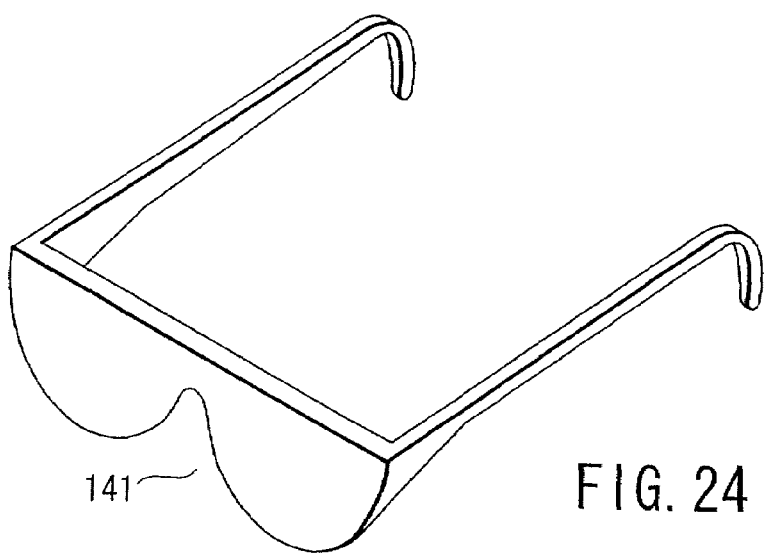
FIG. 24 is a perspective view of an eyeglasses-type display.

In the endoscope system of this embodiment, the control unit 106 is attached to the holding section 105 of the endoscope 100. However, the control unit 106 may be set near the endoscope 100 and connected to the endoscope 100 through a cable. Further, the monitor may be an eyeglasses type display (HMD) 141 as shown in FIG. 24.

FOURTH EMBODIMENT

This embodiment is a modification of the third embodiment, which will be described with reference to FIGS. 25A to 27. The endoscope system of this embodiment comprises an endoscope 200, disposable sheaths 201a and 201b shown in FIG. 25A, a pump unit 202 and a radio unit 203 shown in FIG. 26, and a head-mount display (HMD) 204 shown in FIG. 27. FIG. 25B shows a hemostasis operation using the endoscope, and FIG. 25C shows an inspection state observed through the endoscope.

Figure 25A:
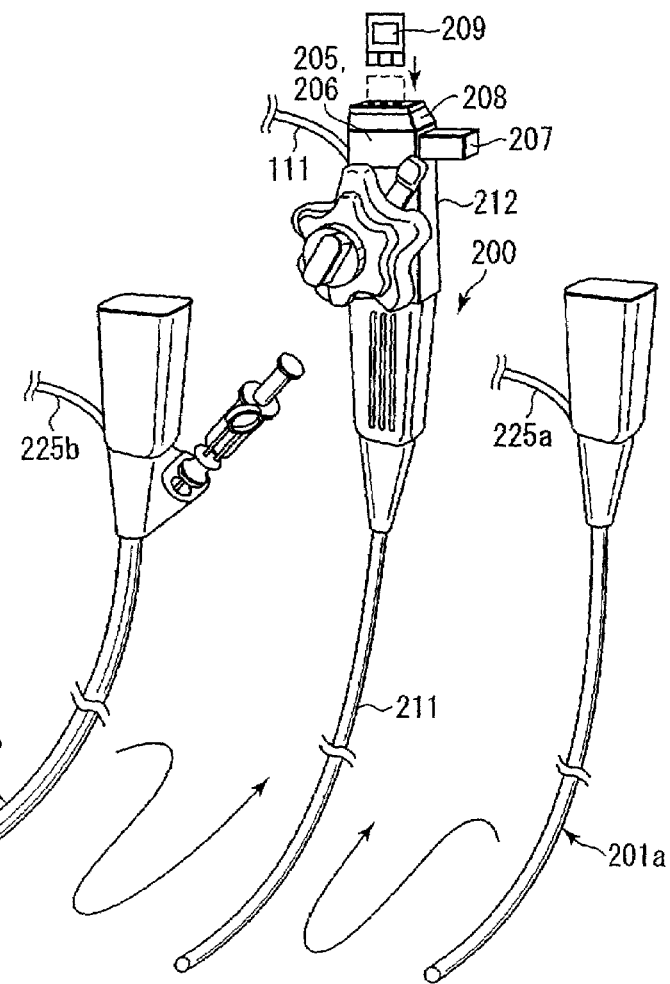
FIG. 25A is a perspective view showing an endoscope and disposable sheaths of an endoscope system according to a modification of the third embodiment.
Figure 25B:
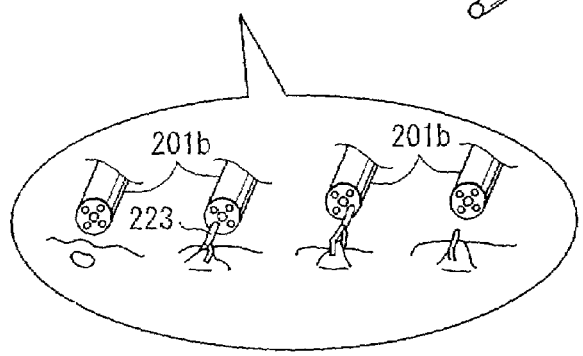
FIG. 25B is an enlarged view of a portion (B) of FIG. 25A, showing a state of a hemostasis operation.
Figure 25C:
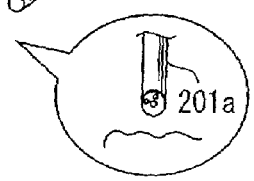
FIG. 25C is an enlarged view of a portion (C) of FIG. 25A, showing an inspection state.

As shown in FIG. 25A, the endoscope 200 comprises an insert section 211 incorporating an image pickup element and an image pickup element driving circuit in its distal end portion. It also comprises an operating section 212 having a unit, which includes an image processor 205 having a signal processing circuit, a light source 206, a battery 207, pump unit driving signal generating means 208 and image storing means 209. The image processor 205, the light source 206, the pump unit driving signal generating means 208 and the image recording means 209 are driven by the battery 207. The image storing means 209 is, for example, a memory card, in which image information can be recorded. The image storing means 209 may be provided in the radio unit 203.

The radio unit 203 is connected to the endoscope 200, the pump unit 202 and the head display 204 via a cable 111.

A signal picked up by the image pickup element of the endoscope 200 is converted to an image signal, and displayed on a monitor 215 of the head-mount display 204 via the radio unit 203. The radio unit 203 can transmit the image signal by radio to a personal computer connected to the LAN or the Internet, if necessary. The radio unit 203 can also receive data from the personal computer and display it on the monitor 215 of the head-mount display 204.

Figure 26:
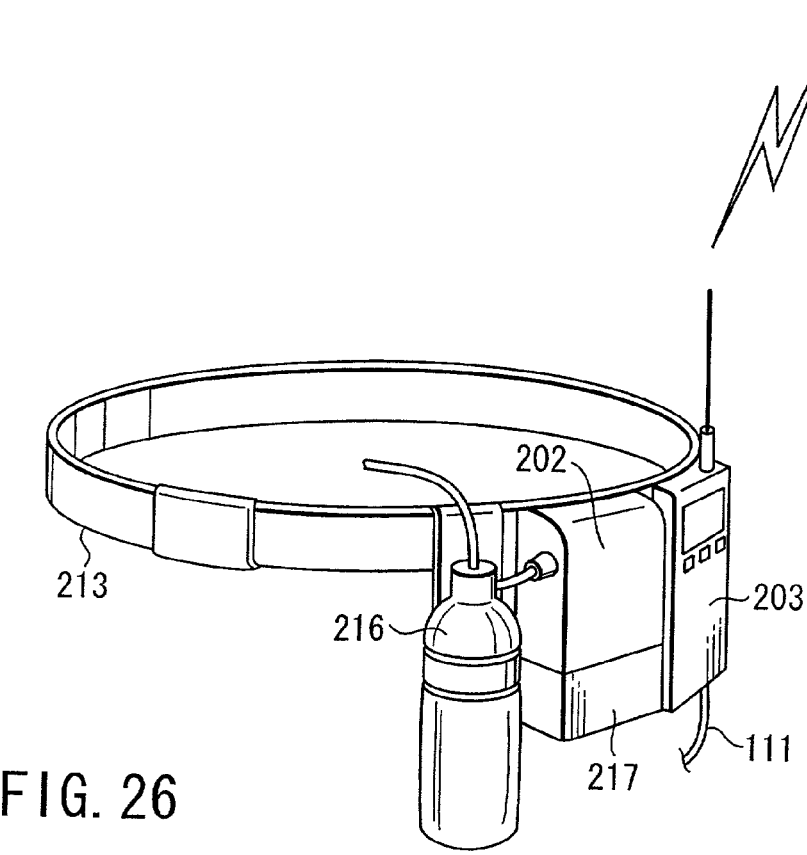
FIG. 26 is a perspective view of a belt, to which a pump unit and a radio unit are attached, in the endoscope system according to the third embodiment.

As shown in FIG. 26, the pump unit 202 has a pump 217 capable of supplying or sucking up air or water. The pump 217 pressurizes the interior of the bottle 216, thereby supplying water from the bottle 216 to the endoscope. When the pump unit driving signal generating means, such as a switch, generates a signal, the signal is transmitted to the pump unit 202 via the radio unit 203. The pump 217 is operated in response to the signal, and supplies or sucks up air or water. The pump unit 202 and the radio unit 203 are detachably attached to a belt 213. The inspector may put on the belt 213, if necessary.

Figure 27:
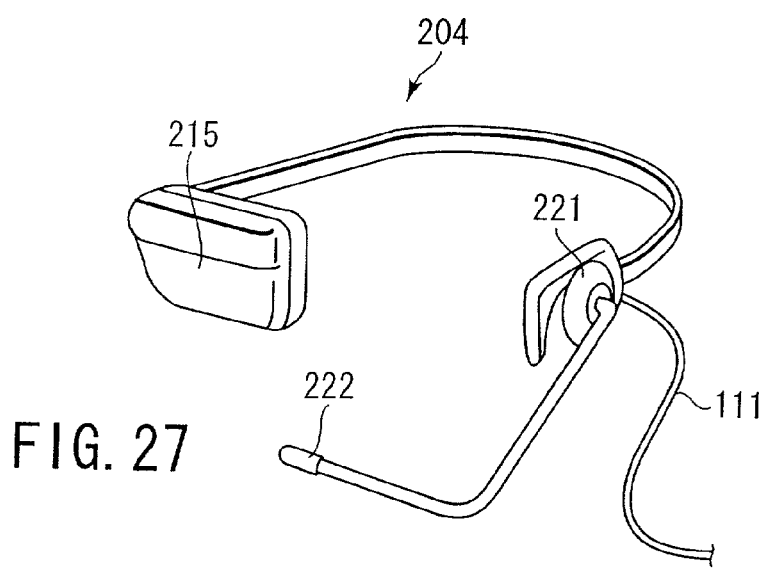
FIG. 27 is a perspective view of a head-mount display of the endoscope system according to the third embodiment.

As shown in FIG. 27, the head-mount display 204 comprises an earphone 221 and a microphone 222, so as to call and communicate with a specific person via the radio unit 203.

A plurality of types of disposable sheaths 201, which are different in diameter and number of channels, are prepared. For example, the disposable sheath 201a arranged on the right portion of FIG. 25A is intended for observation, and comprises two channels: an air/water supplying channel and an air/water sucking channel. The disposable sheath 201b arranged on the left portion of FIG. 25A is intended for hemostasis. It comprises, in addition to the above two channels, a channel for introducing a hypodermic needle for injecting physiological saline and an endoscope treatment tool 223, such as hemostasis clip forceps, into a body cavity.

Tubes 225 are attached to the two channels arranged in each disposable sheath 201, and respectively connected to a water supply bottle and a water suction bottle. The pump unit driving signal generating means supplies an operation signal when necessary, so that an air/water supply or suction operation can be performed.

The image pickup element used in this endoscope system is not limited to a CCD of a solid state image pickup element, but may be a CMOS image made of a photodiode array produced by the CMOS (complementary metal oxide semiconductor) process. The CMOS imager generally has the advantage that it is inexpensive and consumes low power. Further, the image processing circuit and the CMOS imager may be formed on the same wafer. In this case, an additional image processor may not be required. Even if it is required, a compact processor may suffice. Thus, there is a merit of reducing the size and weight of the operating section of the endoscope. Since the image pickup element using the CMOS imager has the aforementioned advantage, it can be naturally used in a disposable video endoscope (flexible scope or rigid scope), a low-price video endoscope and the conventional video scope, as well as in the video endoscope of radio communication type as in the endoscope system of the present invention.

If a white LED (light emitting) is used as the illuminating means of the light source section, a yellow compensating filter is inserted before the image pickup element or the white LED in order to compensate for blue light, which has high emission intensity on the emission spectrum of the white LED. As a result, the light incident on the image pickup element has a uniform color distribution. Thus, it is advantageous in that an image of biological information can be reproduced in a more natural color.

As described above, according to the present invention, it is possible to provide an endoscope system in which a radio communications function is provided, allowing medical treatment to be carried out in understaffed, ill-equipped or difficult conditions, such as in home care or at disaster sites.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
    an endoscope including a section insertable into a body, a holding section to be arranged outside the body and connected to the section insertable into the body to control the same, and an image pickup element which picks up an image inside the body;
    a processing device which processes a signal obtained through the image pickup element and generates an image signal;
    an image display system physically removed from the endoscope;
    a white LED light source arranged in the endoscope;

a color compensating filter, located in front of at least one of the image pickup element and the white LED light source, for compensating for a light component that has high emission intensity in the emission spectrum of the white LED light source; and a data transmitting and receiving device configured to wirelessly transmit and receive data associated with the image signal over a network environment set outside the body; with the image display system receiving the data from the network environment and displaying an image corresponding to the image inside the body picked up by the image pickup element.

2. An endoscope system according to claim 1, wherein the data transmitting and receiving device transmits and receives data in conformity with a standard for bi-directional communications by radio among various apparatuses in a frequency band that can be used without a license.

3. An endoscope system according to claim 1, wherein the processing device includes a memory device having a memory medium for storing the signal obtained through the image pickup element.

4. An endoscope system according to claim 3, wherein the memory medium is detachably inserted in the processing device.

5. An endoscope system according to claim 3, wherein the memory medium includes a writable memory medium.

6. An endoscope system according to claim 3, wherein the memory medium includes a rewritable memory medium.

7. An endoscope system according to claim 3, wherein the memory medium includes a memory card.

8. An endoscope system according to claim 1, wherein the processing device includes a data input/output terminal connected to a network environment.

9. An endoscope system according to claim 1, further comprising an LED light source arranged in the endoscope.

10. An endoscope system according to claim 1, wherein the color compensating filter comprises a yellow compensating filter for compensating for blue.

11. An endoscope system according to claim 1, wherein the image pickup element comprises a CMOS imager.

12. An endoscope system according to claim 1, further comprising wherein the image display system comprises a head-mount display which receives the image signal generated by the processing device via the data transmitting and receiving device and displays an image.

13. An endoscope system according to claim 12, wherein the head-mount display comprises an earphone and a microphone.

14. An endoscope system comprising:
an endoscope including a section insertable into a body, a holding section arranged outside the body and connected to the section insertable into the body to control the same, and an image pickup element which picks up an image inside the body;
a processing device which processes a signal obtained through the image pickup element and generates an image signal;
an image display system physically removed from the endoscope;
a data transmitting and receiving device configured to wirelessly transmit and receive data associated with the image signal over a network environment set outside the body; with
the image display system receiving the data from the network environment and displaying an image corresponding to the image inside the body picked up by the image pickup element;
a radio unit which transmits the image signal generated by the processing device;
a pump to supply and/or suck air and water through the endoscope;
a bottle containing water to be supplied;
a bottle to receive matter sucked up from a body cavity; and
a belt which detachably attaches at least one of the radio unit, the pump and the bottles to an inspector's body.

15. An endoscope system comprising:
an endoscope including a section insertable into a body, a holding section arranged outside the body and connected to the section insertable into the body to control the same, and an image pickup element which picks up an image inside the body;
a processing device which processes a signal obtained through the image pickup element and generates an image signal;
an image display system physically removed from the endoscope;
a data transmitting and receiving device configured to wirelessly transmit and receive data associated with the image signal over a network environment set outside the body; with
the image display system receiving the data from the network environment and displaying an image corresponding to the image inside the body picked up by the image pickup element;
a radio unit which transmits image data obtained by the image pickup element;
a pump to supply and/or suck air and water through the endoscope;
a bottle containing water to be supplied;
a bottle to receive matter sucked up from a body cavity; and
a belt which detachably attaches at least one of the radio unit, the pump and the bottles to an inspector's body.

16. An endoscope system comprising:
an electronic endoscope including an insert section having a distal end portion to be inserted in a body, an image pickup element arranged at the distal end portion, and a holding section which is connected to the insert section, to be arranged outside the body and held by an inspector; and
a control unit detachably attached to the holding section, the control unit comprising:
a light source device which is introduced into the body along with the endoscope and emits illuminating light for illuminating an inside of the body, wherein the light source device is a white LED light source arranged in the endoscope;
a color compensating filter, located in front of at least one of the image pickup element and the white LED light source, for compensating for a light component that has high emission intensity in the emission spectrum of the white LED light source;
a processing device which processes an image signal obtained by the image pickup element and generates image data;
a data transmitting device configured to transmitting by radio the image data generated by the processing device; and an image display system receiving the image data by radio and displaying an image corresponding to the image signal obtained by the image pickup element.

17. An endoscope system according to claim 16, wherein the data transmitting device transmits and receives data in conformity with a standard for bi-directional communications by radio among various apparatuses in a frequency band that can be used without a license.

18. An endoscope system according to claim 16, wherein the processing device includes a memory device having a memory medium for storing the image data.

19. An endoscope system according to claim 18, wherein the memory medium is physically detachably inserted in the processing device.

20. An endoscope system according to claim 18, wherein the memory medium includes a writable memory medium.

21. An endoscope system according to claim 18, wherein the memory medium includes a rewritable versatile memory medium.

22. An endoscope system according to claim 18, wherein the memory medium includes a memory card.

23. An endoscope system according to claim 16, wherein the processing device includes a data input/output terminal connected to a network environment.

24. An endoscope system according to claim 16, further comprising an LED light source arranged in the endoscope.

25. An endoscope system according to claim 16, wherein the color compensating filter comprises a yellow compensating filter for compensating for blue.

26. An endoscope system according to claim 16, wherein the control unit includes a memory device for storing a signal obtained by the image pickup element.

27. An endoscope system comprising:
an electronic endoscope including an insert section having a distal end portion to be inserted in a body, a holding section to be arranged outside the body, which is connected to the insert section, an image pickup element arranged at the distal end portion, a white LED light source arranged in the endoscope, and a color compensating filter, located in front of at least one of the image pickup element and the white LED light source, for compensating for a light component that has high emission intensity in the emission spectrum of the white LED light source; and
a processor unit mountable on a side portion of a subject's bed,
the processor unit comprising:
a processing device which processes a signal obtained by the image pickup element and generates image data;
an image display system physically removed from the endoscope;
a data transmitting and receiving device for wirelessly transmitting and receiving by radio the image data generated by the processing device to and from a network environment; and
the image display system receiving the data from the network environment and displaying an image corresponding to the signal obtained by the image pickup element.

28. An endoscope system according to claim 27, wherein the data transmitting and receiving device transmits and receives data in conformity with a standard for bi-directional communications by radio among various apparatuses in a frequency band that can be used without a license.

29. An endoscope system according to claim 27, wherein the processing device includes a memory device having a memory medium for storing the signal obtained through the image pickup element, and the memory medium is physically detachably inserted in the processing device.

30. An endoscope system according to claim 29, wherein the memory medium includes a writable memory medium.

31. An endoscope system according to claim 29, wherein the memory medium includes a rewritable versatile memory medium.

32. An endoscope system according to claim 29, wherein the memory medium includes a memory card.

33. An endoscope system according to claim 27, wherein the processing device includes a data input/output terminal connected to a network environment.

34. An endoscope system according to claim 27, further comprising an LED light source arranged in the endoscope.

35. An endoscope system according to claim 27, wherein the color compensating filter comprises a yellow compensating filter for compensating for blue.

36. An endoscope system according to claim 27, wherein the image pickup element comprises a CMOS imager.

37. An endoscope system according to claim 27, wherein the image display system comprises a head-mount display having a receiving device for receiving the image signal, and an earphone and a microphone which allow conversation.

38. An endoscope system comprising:
an electronic endoscope including an insert section having a distal end portion to be inserted in a body, a holding section arranged outside the body, which is connected to the insert section, and an image pickup element arranged at the distal end portion; and
a processor unit mountable on a side portion of a subject's bed,
the processor unit comprising:
a processing device which processes a signal obtained by the image pickup element and generates image data;
an image display system physically removed from the endoscope;
a data transmitting and receiving device for wirelessly transmitting and receiving by radio the image data generated by the processing device to and from a network environment; with
the image display system receiving the data from the network environment and displaying an image corresponding to the signal obtained by the image pickup element;
a radio unit which transmits image data obtained by the image pickup element;
a pump to supply and/or suck air and water through the distal end portion of the endoscope;
a bottle containing water to be supplied; and
a bottle to receive matter sucked up from a body cavity,
at least one of the radio unit, the pump and the bottles being detachably attached to an inspector's waist portion.

* * * * *